United States Patent [19]
Pan et al.

[11] Patent Number: 5,849,793
[45] Date of Patent: Dec. 15, 1998

[54] HIV MATRIX PROTEIN TYROSINE POSITION 29 POCKET BINDERS

[75] Inventors: Senliang Pan, Flushing; Michael Bukrinsky, Glenwood Landing, both of N.Y.; Omar K. Haffar, Seattle, Wash.

[73] Assignee: The Picower Institute for Medical Research, Manhasset, N.Y.

[21] Appl. No.: 911,883

[22] Filed: Aug. 15, 1997

[51] Int. Cl.$^6$ .......................... A61K 31/22; C07C 321/00
[52] U.S. Cl. .......................... 514/546; 514/545; 514/544; 560/51; 560/10; 560/9
[58] Field of Search .................................. 560/51, 9, 10; 514/544, 545, 6

[56] References Cited

U.S. PATENT DOCUMENTS

| | | |
|---|---|---|
| 2,553,647 | 5/1951 | Fieser et al. . |
| 2,572,946 | 10/1951 | Paulshock . |
| 3,914,264 | 10/1975 | Marsico, Jr. et al. . |
| 4,053,634 | 10/1977 | Bellina et al. . |
| 4,229,478 | 10/1980 | Jones et al. . |
| 4,929,642 | 5/1990 | Lindner et al. .......................... 514/544 |

OTHER PUBLICATIONS

Chem. Abs. 113: 208214, Khalil et al, "Synthesis and Antimicrobial Evaluation of Novel Thionaiedo derivatives of 1,4–napthoquinones", 1990.

Chem. Abs. 108: 111939 Habib et al, "Synthesis and Antimicrobial Testing of Substituted ((amino carbonyl)methyl)thio)Napthoquinones", 1987.

Chem. Abs. 94:191985, Xi et al, "Studies on Antiasthmatic agents", 1980.

Chem. Abs. 90:203631, Maruyama et al, "Oxidation of 2,5–dimethoxy–acetophenone Derivatives with Thallium (III) Nitrate . . . ", 1978.

Nadler et al., *J. Biol. Chem.*, 272:4310–4315, 1997.

Bukrinsky et al., *Proc. Natl. Acad. Sci. USA* 90:6125–6129, 1993.

Popov et al., *Proc. Natl. Acad. Sci. USA* 93:11859–11864, 1996.

Dubrovsky et al., *Mol. Med.* 1:217–230, 1995.

Bukrinskaya et al., *Proc. Natl. Acad. Sci. USA* 93:367–371, 1996.

Gulizia et al., *J. Virology* 68:2021–2025, 1994.

Gallay et al., *J. Virology* 70:1027–1032, 1996.

Gallay et al, *Cell* 80:379–388, 1995.

Gallay et al., *Cell* 83:569–576, 1995.

Von Schwedler et al., *Proc. Natl. Acad. Sci. USA* 91:6992–6996, 1994.

*Primary Examiner*—Deborah C. Lambkin
*Attorney, Agent, or Firm*—Jeffrey B. Oster

[57] ABSTRACT

There is disclosed a structural genus of compounds, defined according to coordinates in three-dimensional space, that binds amino moieties on neighboring lysine residues in a tyrosine residue 29 pocket of the matrix protein component of the HIV preintegration complex (PIC), thereby preventing the PIC from binding to karyopherin α and preventing nuclear importation and integration of the HIV viral genome into the host cell DNA, thereby preventing viral infection.

15 Claims, 6 Drawing Sheets

HIV MATRIX PROTEIN TYROSINE POSITION 29 POCKET BINDERS

TECHNICAL FIELD OF THE INVENTION

The present invention provides a structural genus of compounds, defined according to coordinates in three-dimensional space, that binds amino moieties on neighboring lysine residues in a tyrosine residue 29 pocket of the matrix protein component of the HIV preintegration complex (PIC), thereby preventing the PIC from binding to karyopherin α and preventing nuclear importation and integration of the HIV viral genome into the host cell DNA, thereby preventing viral infection.

BACKGROUND OF THE INVENTION

In the past decade, infection with the human immunodeficiency virus-type 1 (HIV-1) has reached pandemic proportions. In addition to the overwhelming increase in the number of people infected with HIV-1 in sub-Saharan Africa, there has been a significant increase in new infections in Europe and North America. Of equal concern is the emergence of HIV-1 in southeast Asian countries such as Thailand and Malaysia. Based on the current rate of infection, it is estimated that southeast Asia may, in the near future, surpass Africa as the hot spot of the world. Therefore, infection with HIV-1 and development of AIDS proceeds unabated. In the absence of a protective vaccine, post-infection therapy is the only management tool available to the health care providers.

The identification of long term non-progressors strongly suggested that therapy for HIV-1 infection may delay the onset of disease following infection. To date, the principle targets for HIV-1 therapy have been the viral enzymes, reverse transcriptase and protease, that are important for the virus life cycle. Inhibitors of either of these enzymes successfully reduced the virus load in patients and resulted in increase in the CD4+T lymphocyte subset and have become commercially-available drugs for HIV infection treatment. Both of these end points have been shown to be good correlates for positive prognosis. Importantly, combination therapies utilizing RT inhibitors together with the protease inhibitors in a variety of regimens resulted in reduction of the circulating virus in the blood to below detectable levels. These clinical results showed that maintenance therapy for HIV-1 infection and AIDS is achievable.

However, emergence of virus isolates resistant to the applied anti-viral drugs, as well as cross resistance to multiple drugs within a class of inhibitors is predicted to limit the application of combination therapy. These results strongly indicated the need for continued novel drug development, and continued identification of novel targets, other than the virus enzymes.

Human immunodeficiency virus type-1 (HIV-1) and other lentiviruses infect non-dividing terminally differentiated cells such as primary macrophages (Gendelman et al., *J. Virol.* 58:67–74, 1986;, Gartner et al., *Science* 233:215–219, 1986), primary blood dendritic cells (Langhoff et al., *Proc. Natl. Acad. Sci. USA* 88:998–8002, 1991), and epidermal Langerhan's cells (Ramazzotti et al., *Immunology* 85:94–98, 1995). This is facilitated by the active importation of the HIV-1 preintegration complex (PIC), which incorporates the viral genome, across the intact nuclear envelope of the non-dividing cell (Bukrinsky et al., *Proc. Natl. Acad. Sci. USA* 89:6580–6584, 1992; Bukrinsky et al., *Nature* 365:666–669, 1993; and von Schwedler et al., *Proc. Natl. Acad. Sci. USA* 91:6992–6996, 1994). In addition, HIV-1 can establish productive infection in activated primary T cells at all steps of the cell cycle, prior to and including the M phase, when dissolution of the nuclear envelope occurs. Thus, active nuclear importation obviates the requirement for cell division, thus allowing HIV-1 to infect non-proliferating as well as proliferating cells (Lewis et al., *EMBO J.* 11:3053–3058, 1992), the usual targets of retroviruses (Roe et al., *EMBO J.* 12:2099–2108, 1993; and Lewis and Emerman, *J. Virol.* 68:510–516, 1994).

In addition to the viral genomic RNA the PIC is composed of the gag-derived matrix protein (MA) and the nucleocapsid protein (NC), the reverse transcriptase (RT), integrase (IN), and vpr. Reverse transcription and production of the nascent cDNA is completed in context of the PIC in the cytoplasm of target cell, prior to nuclear entry. It was recently shown (Gallay et al., *J. Virol.* 70:1027–1032, 1996; and Popov et al., *Proc. Natl. Acad. Sci. USA* 93:11859–11864, 1996) that the PIC of HIV-1 associates with karyopherins, the cellular proteins involved in active nuclear importation (reviewed in Adam, *Trends Cell Biol.* 5:189–191, 1995). Karyopherin α binds to target proteins via their nuclear localization sequence (NLS), while karyopherin β mediates docking of the karyopherin α-target protein complex to nuclear pore structures (Radu et al., *Proc. Natl. Acad. Sci. USA* 92:1769–1773, 1995; Moroianu et al., *Proc. Natl. Acad. Sci USA* 92:2008–2011, 1995; Görlich et al., *Nature (London)* 377:246–248, 1995; Adam and Gerace, *Cell* 66:837–847, 1991; Görlich and Mattaj, *Science* 271:1513–1518, 1996; and Hurt, *Cell* 84:509–515, 1996).

HIV-1 matrix protein (MA) contains one defined ($K^{26}KKYK$) and one putative ($K^{110}SKKK$) NLS, and represents a major karyophilic structure within the PIC (Bukrinsky et al., *Nature* 365:666–669, 1993; von Schwedler et al., *Proc. Natl. Acad. Sci. USA* 91:6992–6996, 1994; Gallay et al., *J. Virol.* 70:1027–1032, 1996; and Bukrinsky et al. *Proc. Natl. Acad. Sci. USA* 90:6125–6129, 1993). Synthetic peptides encompassing either of the two MA NLS bound both identified human karyopherin α present in B cell and T cell lysates (Nadler et al., *J. Biol. Chem.* 272, 4310–4315, 1997). Mutations in the KKKYK NLS of MA, alone or in combination with the deletion of Vpr, reduced nuclear importation of the HIV-1 PIC and inhibited infection of primary macrophage cultures (von Schwedler et al., *Proc. Natl. Acad. Sci. USA* 91:6992–6996, 1994; Heizinger et al., *Proc. Natl. Acad. Sci.* 91:7311–7315, 1992), as well as growth-arrested T cells (Bukrinsky et al., *Nature* 365:666–669, 1993) and CD4+-HeLa cell cultures (Emerman et al., *Nature (London)* 369:107–108, 1994). Single amino acid substitutions within the KKKYK NLS also reduced binding of the HIV-1 PIC to yeast karyopherin α in vitro (Popov et al., *Proc. Natl. Acad. Sci. USA* 93:11859–11864, 1996), thus providing a link between binding of PIC to karyopherin α, nuclear import, and viral replication in non-dividing cells.

SUMMARY OF THE INVENTION

The present invention provides a compound having the formula I:

3

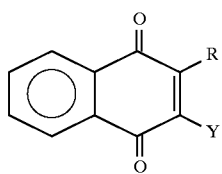

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain). Preferably, X is $(CH_2)_n$, is 2, Z is methoxy, and Y is H.

The present invention further provides a pharmaceutical composition comprising a compound of formula I and a pharmaceutically acceptable carrier.

The present invention also provides a method for treating HIV infection, comprising administering an effective amount of a compound from formula I.

The present invention farther provides a combination therapeutic treatment regimen for the treatment of HIV infection, comprising a compound of formula I:

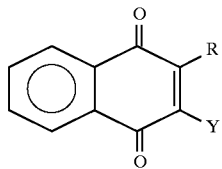

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain), and a reverse transcriptase inhibitor. Preferably, the reverse transcriptase inhibitor is selected from the group consisting of 3TC, AZT, ddI, d4T, ddC, and combinations thereof. Preferably, in formula I, X is $(CH_2)_n$, is 2, Z is methoxy, and Y is H. Preferably, the combination further comprises an HIV protease inhibitor. The HIV protease inhibitor is selected from the group consisting of ritonavir, nelfinavir, saquinavir, indinavir, and combinations thereof.

DETAILED DESCRIPTION OF THE INVENTION

Figure 1:
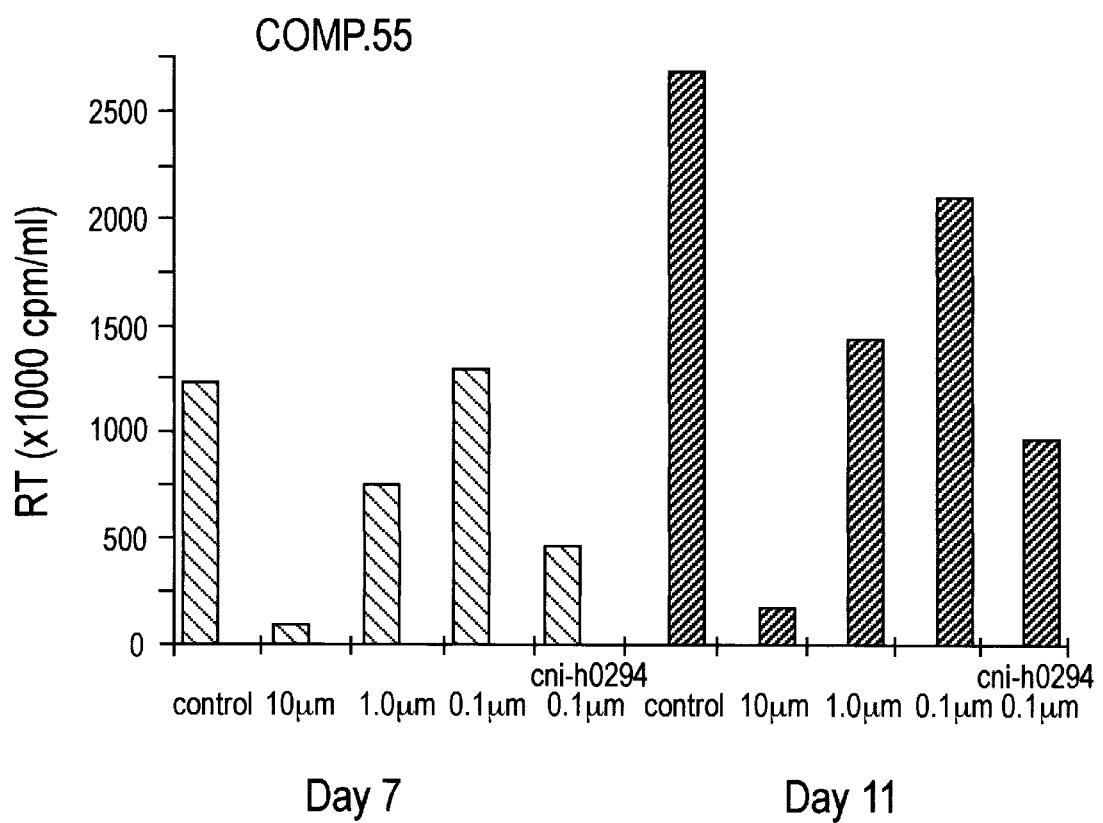
FIG. 1 shows a graph comparing inventive compound 55 (1,4-naphthoquinone-2-propionic acid) with a structurally dissimilar compound ("cni-h0294") having a positive charge in a pyrimidine ring moiety. The assay measures reverse transcriptase activity in the infected macrophage culture supernatants as a measure of virus production. These data can be directly correlated to efficacy treating HIV infection. These data show that inventive compound 55 was efficacious and showed a dose-response relationship. However cni-h0294 showed more potent activity at the 0.1 μm drug concentration at both day 7 and day 11 measurements.

The present invention provides a compound having the formula I:

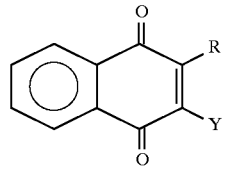

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain). Preferably, X is $(CH_2)_n$ is 2, Z is methoxy, and Y is H.

The present invention further provides a pharmaceutical composition comprising a compound of formula I and a pharmaceutically acceptable carrier.

The present invention also provides a method for treating HIV infection, comprising administering an effective amount of a compound from formula I.

Compound Synthesis

The illustrative compounds can be synthesized by common organic synthesis techniques. Illustrative compound 55 is 1,4-naphthoquinone-2-propionic acid. Compound 55 was synthesized by adding naphthoquinone (6.32 g), succinic acid (14.2 g) and silver nitrate (2 g) in a solution of water-acetonitrile (3:1 by weight). The mixture was heated to the 65°–75° C. range and stirred and ammonium persulfate (12 g) in water (50 ml) was added dropwise over 25 min. After addition, the reaction was maintained at 60° C. for 15 min, then cooled in ice. The reaction product was then extracted with ether (2×100 ml), with the ether layers extracted with 2×100 ml 5% aqueous sodium bicarbonate (with foaming). The ether layers were discarded. Each bicarbonate extract was rapidly added to a pH 3.5 phosphate buffer solution due to the instability of the carboxylate anion form of the product (results in rapid darkening). The pH 3.5 mixture was then extracted with ether and the extracts were washed in brine and then concentrated in vacuo to a brown solid. The solid was stirred with 30 ml benzene and then filtered. The filter cake was then taken up in hot benzene and then filtered, On cooling, the filtrate deposited 2.5 g of 1,4-naphthoquinone-2-propionic acid as yellow needles having a melting point of 138° C.

Illustrative compound 59 is 1,4-naphthoquinone-2-propionic acid methyl ester. This compound was synthesized by obtaining naphthoquinone (15.8 g, Aldrich) and monomethyl succinate (31 g) in 3:1 water-acetonitrile (500 ml) and heating the mixture to about 80° C. Silver nitrate (5 g) was added, followed by a solution of ammonium persulfate (30 g) in water (120 ml) added dropwise over about 80 minutes, while the temperature was slowly lowered to about 65° C. The mixture was stirred an additional 20 minutes at 65° C., then cooled to about 10° C. The mixture was extracted with 2×300 ml ether and 100 ml dichloromethane. The combined extracts were dried over magnesium sulfate and decolorized with carbon. After filtration and further concentration, the product was about 20 g of a red-brown oil. The product was chromatographed on 200 g silica gel with a gradient of 0–100% chloroform in benzene, followed by 5% tetrahydrofuran in chloroform. The fractions containing mostly desired product were combined and recrystalized from methanol to give pure compound having Rf 0.2 (1:1 chloroform:benzene) with a melting point of 79.5° C.

Pharmaceutical Formulation

The inventive pharmaceutical complex or inventive pharmaceutical combination can be administered to a patient either by itself (complex or combination) or in pharmaceutical compositions where it is mixed with suitable carriers and excipients. The inventive compound or pharmaceutical composition can be administered parenterally, such as by intravenous injection or infusion, intraperitoneal injection, subcutaneous injection, or intramuscular injection. The inventive compound or pharmaceutical composition can be administered orally or rectally through appropriate formulation with carriers and excipients to form tablets, pills, capsules, liquids, gels, syrups, slurries, suspensions and the like. The inventive compound or pharmaceutical composition can be administered topically, such as by skin patch, to achieve consistent systemic levels of active agent. The inventive compound or pharmaceutical composition is formulated into topical creams, skin or mucosal patch, liquids or gels suitable to topical application to skin or mucosal membrane surfaces. The inventive compound or pharmaceutical composition can be administered by inhaler to the respiratory tract for local or systemic treatment of HIV infection.

The dosage of the inventive compound or pharmaceutical composition suitable for use with the present invention can be determined by those skilled in the art from this disclosure. The pharmaceutical composition will contain an effective dosage (depending upon the route of administration and pharmacokinetics of the active agent) of the inventive compound or pharmaceutical composition and suitable pharmaceutical carriers and excipients, which are suitable for the particular route of administration of the formulation (i.e., oral, parenteral, topical or by inhalation). The active compound is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active complex or combination in water-soluble form. Additionally, suspensions of the active compound may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active compound with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a desintegrating agent may be added, and a stabilizer may be added.

EXAMPLE 1

This example illustrates several in vitro experiments in predictive models of treatment of HIV infection to show the therapeutic utility of the inventive compounds. Primary macrophage cultures were obtained from peripheral blood mononuclear cells (from normal or uninfected human donors) were isolated by the separation on Ficoll-hypaque (Pharmacia), and plated at $8 \times 10^6$ cells/ml in Dulbecco's Modified Eagle's Medium (DMEM) supplemented with 10% heat-inactivated normal human serum (NHS). After adherence for 2 hours at 37° C., the nonadherent cells were discarded and the adherent macrophages were collected and cultured for seven days in DMEM supplemented with macrophage colony stimulating factor (MCSF) at $1 \times 10^6$ cells/ml. The cells were then infected with the macrophages tropic clinical isolate HIV-$1_{ADA}$ with MOI of $200 \times 10^3$ cpm/$10^6$ cells in the presence of various concentrations of test drug. Specifically, compound 59 was dissolved in DMSO as indicated. After 2 hours at 37° C., free virus was washed away and the cells were cultured in fresh DMEM/10% NHS in the presence of the test drugs. Half the volume of culture medium was changed every 3–4 days and the level of virus in the medium assayed on days 7 and 11 following infection by quantitating the level of virus associated reverse transcriptase according to the procedures described in Dubrovsky et al., *Molec. Med.* 1:217–230, 1995.

Primary macrophage cultures were infected with HIV-1. Compound (55 in FIG. 1 or 59 in FIG. 2) was added at differing concentrations. In addition, a positive control compound (called "cni-h0294") was added at the concentration indicated. After a two hour adsorption, excess viruses or pseudovirons were washed away, and the cells were incubated for indicated intervals prior to analysis. RT, or reverse transcriptase activity, was measured by standard techniques.

FIG. 1 shows a graph comparing anti-HIV therapeutic activity of inventive compound 55 with another nuclear importation inhibitor that acts by binding to the preintegration complex ("cni-h0294" described in U.S. Pat. No. 5,574,040, the disclosure of which is incorporated by reference herein.) having a positive charge in a pyrimidine moiety in an assay of anti-HIV activity in macrophage cultures. The assay measures reverse transcriptase activity in the infected macrophage culture supernatants as a measure of virus production. These data can be directly correlated to efficacy treating HIV infection. These data show that inventive compound 55 demonstrated therapeutic activity in a predictive model of anti-HIV anti-infectivity activity.

Figure 2:
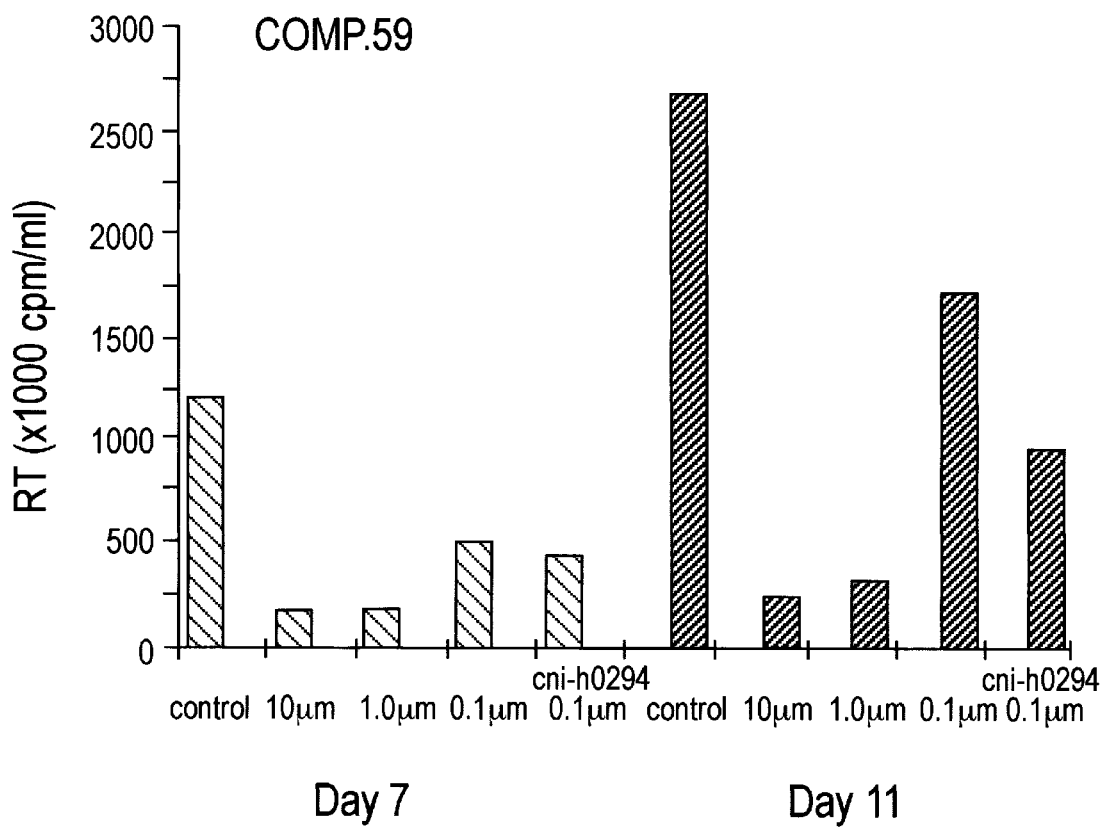
FIG. 2 shows a graph comparing inventive compound 59 (1,4-naphthoquinone-2-propionic acid methyl ester) with a structurally dissimilar compound ("cni -h0294") having a positive charge in the pyrimidine moiety. The assay measures reverse transcriptase activity in the infected macrophage culture supernatants as a measure of virus production. These data can be directly correlated to efficacy treating HIV infection. These data show that inventive compound 59 was efficacious and showed a dose-response relationship. However cni-h0294 showed more potent activity at the 0.1 μm drug concentration at the day 11 measurement.

FIG. 2 shows a graph comparing anti-HIV therapeutic activity of inventive compound 59 with another preintegration complex inhibitor ("cni-h0294") having a positive charge in a pyrimidine moiety in an assay of anti-HIV activity in macrophage cultures. The assay measures reverse transcriptase activity in the infected macrophage culture supernatants as a measure of virus production. These data can be directly correlated to efficacy treating HIV infection. These data show that inventive compound 59 demonstrated therapeutic activity in a predictive model of anti-HIV anti-infectivity activity.

EXAMPLE 2

This example illustrates the therapeutic activity of the combination of an inventive compound from formula 1 (compound 59) and an illustrative reverse transcriptase inhibitor, 3TC. Peripheral blood mononuclear cells (from normal or uninfected human donors) were isolated by the separation on Ficoll-hypaque (Pharmacia), and plated at $8 \times 10^6$ cells/ml in Dulbecco's Modified Eagle's Medium (DMEM) supplemented with 10% heat-inactivated normal human serum (NHS). After adherence for 2 hours at 37° C., the nonadherent cells were discarded and the adherent macrophages were collected and cultured for seven days in DMEM supplemented with macrophage colony stimulating factor (MCSF) at $1 \times 10^6$ cells/ml. The cells were then infected with the macrophages tropic clinical isolate HIV-$1_{ADA}$ with MOI of $200 \times 10^3$ cpm/$10^6$ cells in the presence of various concentrations of test drug. Specifically, compound 59 was dissolved in DMSO as indicated. After 2 hours at 37° C., free virus was washed away and the cells were cultured in fresh DMEM/10% NHS in the presence of the test drugs. Half the volume of culture medium was changed every 3–4 days and the level of virus in the medium assayed on days 7 and 11 following infection by quantitating the level of virus associated reverse transcriptase according to the procedures described in Dubrovsky et al., *Molec. Med.* 1:217–230, 1995.

Figure 3:
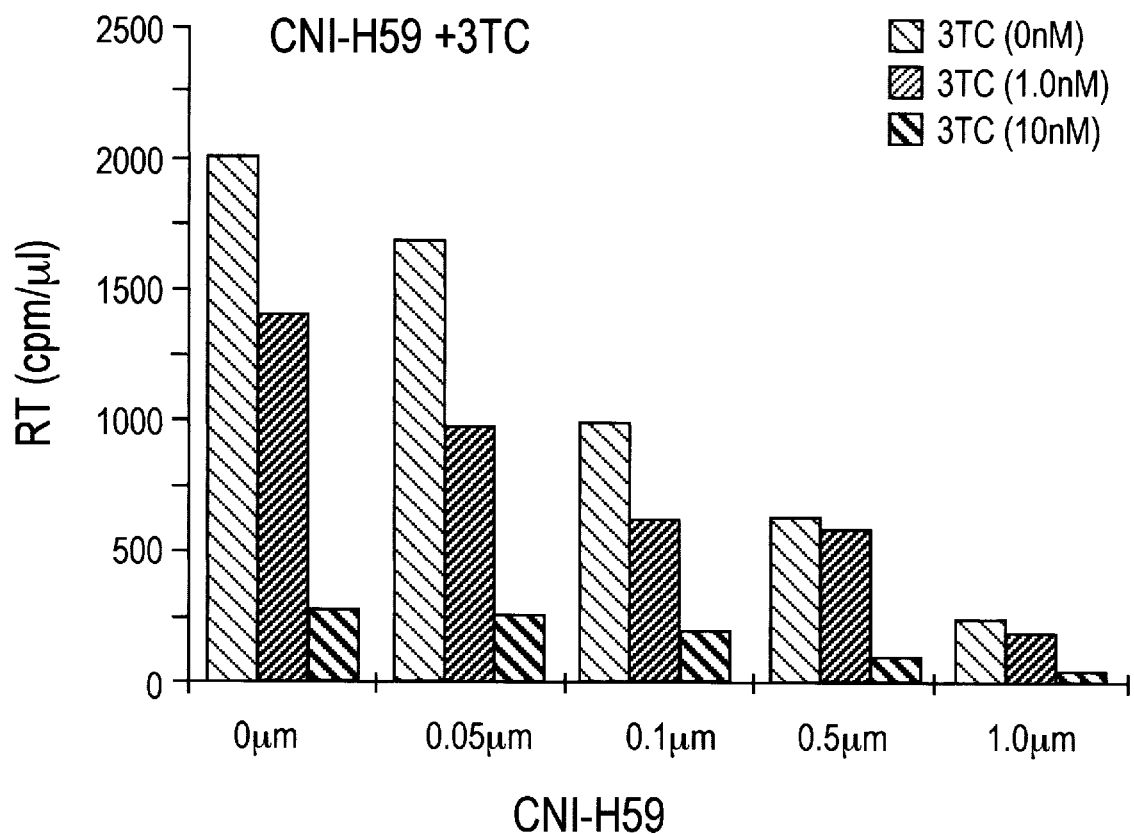
FIG. 3 shows a graph comparing inventive compound 59 alone and with the reverse transcriptase inhibitor 3TC for combination anti-HIV anti-infective therapy in a predictive assay. The assay measures reverse transcriptase activity in primary macrophage cultures as a measure of virus production. These data can be directly correlated to efficacy treating HIV infection. These data show that inventive compound 59 was efficacious and showed a dose-response relationship. These data also show that the anti-infective properties of compound 59 are at least additive and possibly synergistic with the reverse transcriptase inhibitor 3TC.

Various concentrations of compound 59 were tested alone or with two concentrations of the reverse transcriptase inhibitor 3TC (BioChem Pharma, Laval, Quebec). The data reported in FIG. 3 show additive to synergistic activity of this important combination of an inventive preintegration complex inhibitor, compound 59, and an exemplary reverse transcriptase (RT) inhibitor. Moreover, these data further show the effectiveness of a combination therapeutic of a preintegration complex inhibitor and a RT inhibitor.

EXAMPLE 3

Figure 4:
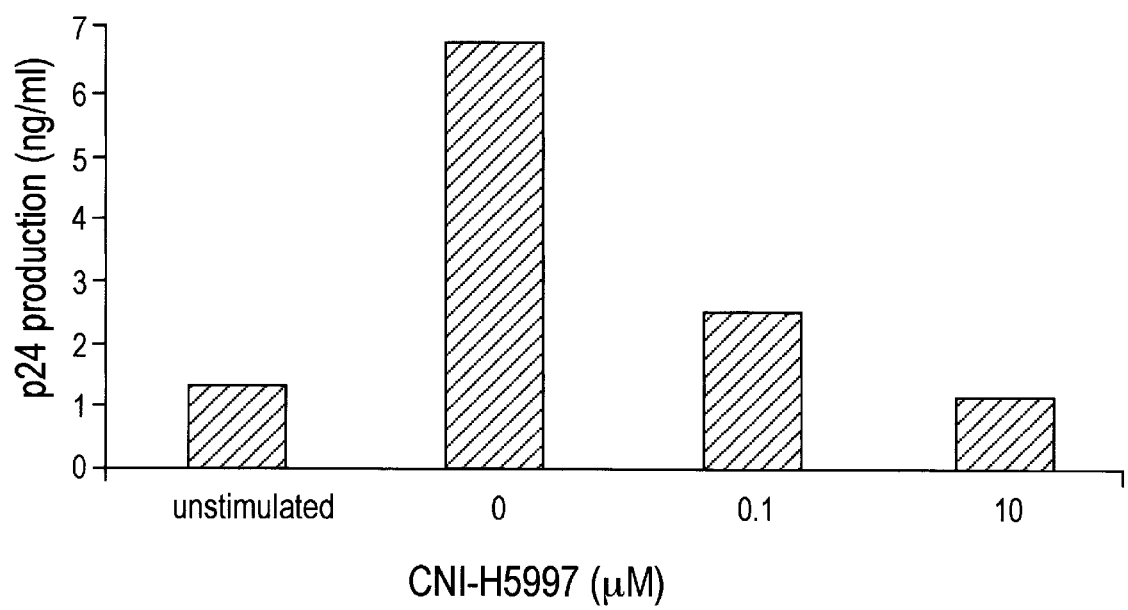
FIGS. 4 and 5 show a dose-response relationship for compound 59 having anti-infective therapeutic activity in human PBMCs for an uninfected donor activated with anti-CD3 and anti-CD28 mAbs in the presence of compound prior to infection with HIV-1 virus. Compound 59 demonstrated therapeutic activity and a dose-response relationship in this predictive model for HIV anti-infective therapeutic activity.
Figure 5:
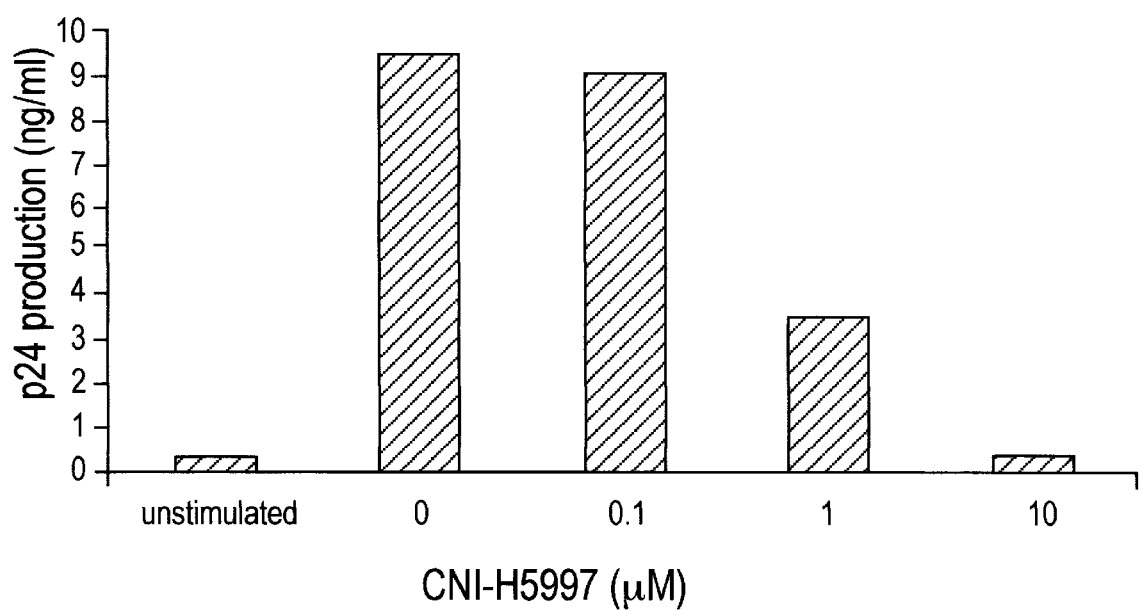

This example illustrates that compound 59 inhibits HIV-1 virus replication in acutely infected PBMC cultures activated with anti-CD3 and anti-CD28 monoclonal antibodies (FIGS. 4 and 5). Peripheral blood mononuclear cells were isolated from an uninfected individual and depleted of CD8+ T lymphocytes using a CD8-specific monoclonal antibody, according to the procedure described by Smithgall et al., *J. Immunol.* 156:2324–2330, 1996. Briefly, the procedure substitutes separation with magnetic beads for complement mediated lysis of antibody bound cells. The remaining PBMC fractions were suspended in RPMI culture medium supplemented with 10% heat-inactivated human serum at $2 \times 10^6$ cells/200 µl. Cells were activated with anti-CD3 mAb (1 µg/ml) together with anti-CD28 mAb (1 µg/ml) in the presence of various concentrations of compound 59. This form of cell activation specifically targets CD4+ T lymphocytes in the population.

Cells were pretreated with antibody and test compound for 2–3 hours prior to addition of the virus inoculum. The virus used in this experiment, HIV-$1_{M1}$, is a patient-derived isolate, and was used at approximately MOI=5 TCID$_{50}$. After 2 hr incubation for adsorption of virus, the cells were washed free of the inoculum, and then resuspended again in 200 µl of culture medium supplemented with anti-CD3 and anti-CD28 mAbs together with varying concentrations of compound 59 (to show a dose-response relationship). Cells were then placed into a U-bottom 96 well culture plate in 4–6 replicates at $1.5 \times 10^5$ cells/replicate/well. Virus production was measured on day 6–10 following infection using p24 production as an end point. The p24 antigen capture assay was performed according to the manufacturers recommendations.

The data presented in FIGS. 4 and 5 show a dose-response relationship at 0, 0.01 µM, 1.0 µM, and 10 µM concentrations of compound 59 ("CNI-H5997") when using p24 as a measure of virus concentration.

Figure 6:
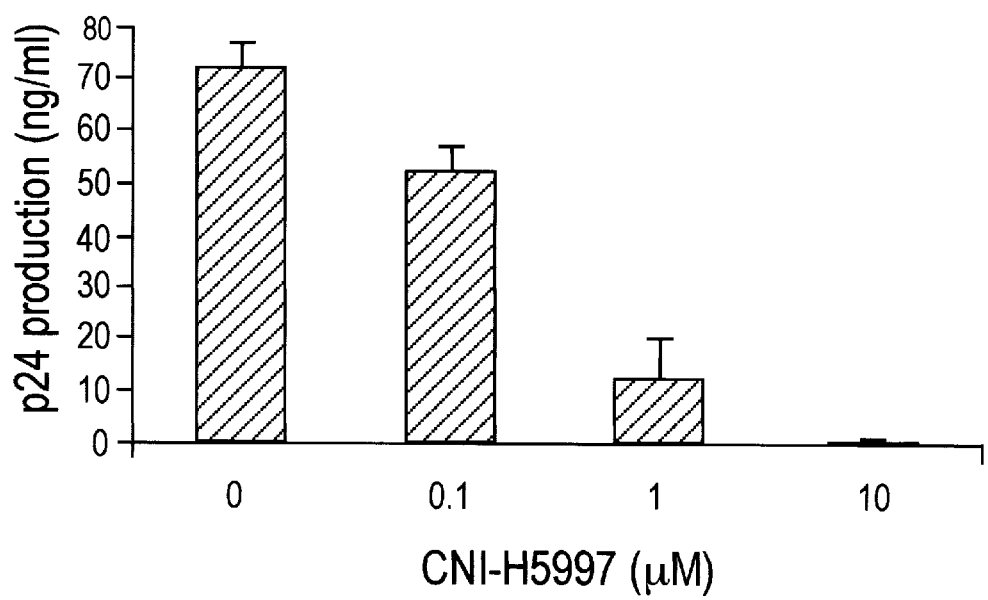
FIG. 6 shows a dose-response relationship for compound 59 having anti-infective therapeutic activity in endogenously-infected PBMCs from an HIV-1 seropositive donor activated with just anti-CD3 mAb in the presence of compound. Compound 59 demonstrated therapeutic activity and a dose-response relationship in this predictive model for HIV anti-infective therapeutic activity.

Compound 59 also inhibited virus replication in PBMC from a HIV-1 infected individual when the PBMCs were activated in vitro with anti-CD3 mAb (FIG. 6). PBMCs from a seropositive individual were collected and depleted of CD8+ T lymphocytes as described above. Cells were suspended in culture medium and activated with anti-CD3 mAb (1 µg/ml). After 6–10 days virus production was evaluated by measuring levels of p24 in the culture supernatants and comparing treated to untreated cultures. FIG. 6 shows a dose-response relationship for compound 59 ("CNI-H5997") under the foregoing experimental conditions in this predictive assay of HIV anti-infective properties.

We claim:

1. A compound having the formula I:

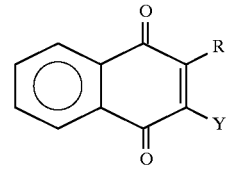

wherein R is —X—CO—Z, wherein Z is $C_{4-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain).

2. A pharmaceutical formulation for the treatment of HIV infection, comprising a compound of formula I:

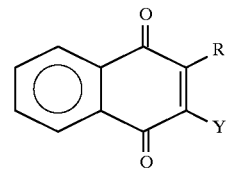

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain), and a pharmaceutically acceptable carrier.

3. The pharmaceutical composition of claim 2 wherein X is $(CH_2)_n$, n is 2, Z is methoxy, and Y is H.

4. A method for treating HIV infection, comprising administering an effective amount of a compound from formula I:

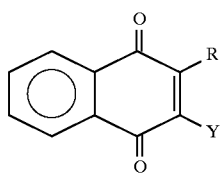

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain), and a pharmaceutically acceptable carrier.

5. The method of claim 4 wherein X is $(CH_2)_n$, n is 2, Z is methoxy, and Y is H.

6. A combination therapeutic treatment regimen for the treatment of HIV infection, comprising a compound of formula I:

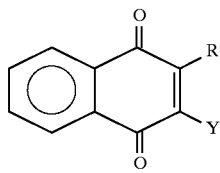

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain), and a reverse transcriptase inhibitor.

7. The combination of claim 6 wherein the reverse transcriptase inhibitor is selected from the group consisting of 3TC, AZT, ddI, d4T, ddC, and combinations thereof.

8. The combination of claim 6 wherein X is $(CH_2)_n$, n is 2, Z is methoxy, and Y is H.

9. The combination of claim 6, further comprising an HIV protease inhibitor.

10. The combination of claim 9, wherein the HIV protease inhibitor is selected from the group consisting of ritonavir, nelfinavir, saquinavir, indinavir, and combinations thereof.

11. A method for treating HIV infection, comprising administering an effective amount of a compound of formula I:

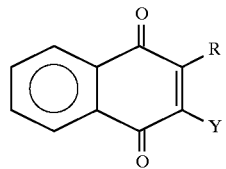

wherein R is —X—CO—Z, wherein Z is $C_{1-6}$ (straight of branched) alkoxy, wherein X is $(CH_2)_n$ or —S—$(CH_2)_n$, wherein n is an integer from 0 to 6, and wherein Y is H or $C_{1-6}$ alkyl (straight or branched chain), and an effective amount of a reverse transcriptase inhibitor.

12. The method of claim 11 wherein the reverse transcriptase inhibitor is selected from the group consisting of 3TC, AZT, ddI, d4T, ddC, and combinations thereof.

13. The method of claim 11 wherein X is $(CH_2)_n$, n is 2, Z is methoxy, and Y is H.

14. The method of claim 11, further comprising an effective amount of an HIV protease inhibitor.

15. The method of claim 14, wherein the HIV protease inhibitor is selected from the group consisting of ritonavir, nelfinavir, saquinavir, indinavir, and combinations thereof.

* * * * *